United States Patent [19]

Okaya et al.

[11] Patent Number: 5,169,630

[45] Date of Patent: Dec. 8, 1992

[54] EXTERNAL SKIN PREPARATION

[75] Inventors: Yoshio Okaya, Ebina; Katsumi Tomoda, Takarazuka; Taihei Hamazaki, Yokohama, all of Japan

[73] Assignees: Pola Chemical Industries, Ltd., Shizuoka; Takeda Chemical Industries, Ltd., Osaka, both of Japan

[21] Appl. No.: 599,357

[22] Filed: Oct. 18, 1990

[30] Foreign Application Priority Data

Oct. 19, 1989 [JP] Japan .................................. 1-270363

[51] Int. Cl.$^5$ ........................ A61K 7/48; A61K 37/50
[52] U.S. Cl. ................................ 424/401; 424/78.37; 424/94.4; 424/70
[58] Field of Search ........................ 424/94.3, 94.4, 70, 424/639, 640, 401, 78.37; 435/189

[56] References Cited

U.S. PATENT DOCUMENTS 2,985,533  5/1961  Zorn ............................. 424/639 X
4,129,644 12/1978  Kalopissis et al. ................ 424/70 X

*Primary Examiner*—Thurman K. Page
*Attorney, Agent, or Firm*—Wenderoth, Lind & Ponack

[57] ABSTRACT

A manganese-containing superoxide dismutase activity of an aqueous external skin preparation which contains (a) manganese-containing superoxide dismutase and/or a modification of manganese-containing superoxide dismutase and (b) a physiologically acceptable water-soluble manganese salt is effective maintained and the aqueous external skin preparation is used for combatting skin-roughening.

5 Claims, No Drawings

EXTERNAL SKIN PREPARATION

FIELD OF THE INVENTION

This invention relates to an aqueous external skin preparation in which the efficacy of manganese-containing superoxide dismutase is retained and the stability thereof is improved.

BACKGROUND OF THE INVENTION

Since 1969, when McCord and Fridovich found that, from a biochemical function viewpoint, superoxide dismutase is an enzyme capable of scavenging active oxygen by catalyzing the reaction: $2O_2.+2H^+ \rightarrow H_2O_2 + O_2$, a large number of studies have been made on the antiinflammatory, pigmentation preventing, autoxidation preventing and, furthermore, aging controlling and anticancer activities of superoxide dismutase.

Manganese-containing superoxide dismutase (hereinafter referred to as "Mn-SOD") has been discovered in eukaryotic cells and in animal and plant mitochondria. It is also known that this Mn-SOD occurs in the human epidermis [cf. e.g. Noritaka Ohkuma et al., Japanese Journal of Dermatology, 92 (5), 583 (1982); Kiyoshi Toda, The Journal of the Japanese Society for Cutaneous Health, No. 8, 38 (1982); Katsuhito Sugiura et al., Japanese Journal of Dermatology, 95 (14), 1535 (1985); N. Ohkuma et al., J. Dermatology, 14, 562 (1987)].

Studies have been conducted also on the production and isolation of Mn-SOD [cf. e.g. Japanese Kokai Tokkyo Koho (published unexamined patent application) 29285/1982; Japanese Patent Publication No. 48514/1988; Reddy, C. D. et al., Biochem. Int., 8 (5), 707 (1984)]. However, Mn-SOD has a drawback in that its enzyme activity decreases in aqueous systems, namely its stability is unsatisfactory.

For achieving an improvement in this respect, attempts have been made to chemically modify Mn-SOD to give modifications of manganese-containing superoxide dismutase (hereinafter referred to as "modified Mn-SOD") [cf. e.g. Japanese Kokai Tokkyo Koho No. 115280/1987; Kazuo Hayano, Kagaku to Kogyo (Chemistry and Industry), 39 (9), 678 (1986); Japanese Patent Publication No. 48514/1988; Koichi Miyata, Monthly Bio/Industry, 5 (7), 494 (1988)]. However, satisfactory results have not been obtained as yet.

Furthermore, several investigations have been carried out so far concerning the stabilization of Mn-SOD or modified Mn-SOD in cosmetic compositions [cf. e.g. Japanese Kokai Tokkyo Koho No. 87712/1980; Japanese Patent Publication No. 44800/1987; Japanese Kokai Tokkyo Koho No. 96107/1989; U.S. Pat. No. 4129644]. Under existing circumstances, however, satisfactory results have not been attained as yet in this respect.

SUMMARY OF THE INVENTION

This invention relates to:
An aqueous external skin preparation which contains (a) manganese-containing superoxide dismutase and/or a modification of manganese-containing superoxide dismutase and (b) a physiologically acceptable water-soluble manganese salt: and production thereof.

DETAILED DESCRIPTION OF THE INVENTION

It is an object of the invention to provide an aqueous external skin preparation which contains Mn-SOD and-/or modified Mn-SOD, with improved reducing potential against skin-roughening by maintain the enzyme activity stably.

The present inventors paid their attention to the fact that manganese is a constituent element of Mn-SOD and of modified Mn-SOD and, considering that the decrease in enzyme activity should be concerned with manganese atom elimination, performed intensive investigations on the combined use of various metal salts or chelating agents and, as a result, found that Mn-SOD and modified Mn-SOD are stable in aqueous systems containing a water-soluble manganese salt in combination with Mn-SOD and/or modified Mn-SOD. The present invention is thus based on such finding and provides a method of stabilizing said enzymes in aqueous systems as well as an aqueous external skin preparation which contains, as essential components thereof, manganese-containing superoxide dismutase and/or a polyalkylene glycol- or polysaccharide-bound modification of manganese-containing superoxide dismutase and a physiologically acceptable water-soluble manganese salt.

In the following, the invention is described in further detail.

The Mn-SOD to be used in the practice of this invention may be of any origin without any particular limitation thereon. Generally, however, microbial Mn-SOD is used, such as the one described in Japanese Kokai Tokkyo Koho No. 29285/1982, for instance.

The modified Mn-SOD to be used in the practice of the invention is derived from the Mn-SOD mentioned above by binding thereto a polyalkylene glycol or polysaccharide either directly or using cyanuric chloride or other polyfunctional agents.

As examples of the polyalkylene glycol in the above case, there may be mentioned polyethylene glycol, polypropylene glycol and ethylene oxide-propylene oxide copolymers.

As the polysaccharide, there may be mentioned dextran, cellulose, inulin and the like, and derivatives of these.

The modified Mn-SOD is produced in the following method. Using the method described in the laid-open official gazette of of European Patent No. 210761, for example, 25 g of polyethylene glycol with an average molecular weight of 1,900 is added to a mixture of 200 ml of benzene, 20 g of anhydrous sodium carbonate and 10 g of molecular sieve 3A (Wako Pure Chemical Industries), 750 mg of cyanuric chloride is further added, resulting mixture is stirred at 80° C. for 20 hours. A precipitate (hereinafter referred to as "activated PEG") is obtained as the reaction product. To 5.0 ml of 0.1 M borate buffer (pH 9.0) are added 15 mg of Mn-SOD derived from *Serratia marcescens* ATCC 21074 and having a potency of 3,600 units/mg and 1.5 g of the above-mentioned activated PEG. After allowing the reaction to proceed at 4° C. for 2 hours, the reaction is stopped by neutralization. The reaction product is purified by column chromatography to give 15 mg of PEG-modified Mn-SOD with a potency of 1,500 units/mg.

Hereinafter this PEG-modified Mn-SOD is referred to as "PEG-Mn-SOD" for short.

It is desirable that, in the practice of the invention, the Mn-SOD and/or modified Mn-SOD is contained in the external skin preparation in an amount of 0.1 to 20,000 units per gram. The potency referred to herein is the one measured by the cytochrome C reduction method of McCord et al. [cf. McCord, J. M. and Fridovich, I., J. Biol. Chem., 244, 6049 (1969)].

When the content as expressed in terms of potency is lower than 0.1 unit/g, the efficacy of the enzyme cannot be manifested to a satisfactory extent. When the content is higher than 20,000 units/g, the improvement in the efficacy of said enzyme cannot correspond to the amount of said enzyme but is rather counterbalanced by unfavorable results such as emission of a characteristic odor.

The manganese salt to be used in accordance with the invention is a physiologically acceptable watersoluble manganese salt which, when dissolved in purified water, gives the manganese ion. Preferred examples include, among others, manganese chloride, manganese acetate and manganese ammonium sulfate.

The content of the manganese salt is preferably within the range of 0.0001 to 10% by weight based on the external skin preparation. At lower concentrations than 0.0001% by weight, the enzyme stabilizing effect becomes insufficiently low while, at concentrations above 10% by weight, adverse effects may be produced, for example coloration of the external skin preparation and/or incompatibility sensation upon application of the preparation.

The term "aqueous external skin preparation" as used herein means a external skin preparation the water content of which is within the range of about 3 to 99%, preferably 5 to 99%, by weight.

The present invention also provides a method of stabilizing Mn-SOD and/or modified Mn-SOD in an aqueous system which comprises a manganese salt in combination with the enzyme or enzymes mentioned above. In this case, the hydrogen ion concentration should preferably be maintained at pH 4.0 to 11.0, more preferably pH 6.0 to 9.0.

EXAMPLE AND COMPARATIVE EXAMPLE

The following examples and comparative examples are further illustrative of the invention.

In these examples and comparative examples, the compounding proportions are given in terms of part(s) by weight.

Examples 1-3 and Comparative Examples 1-4

The skin lotion formulations were prepared and tested in Examples 1, 2 and 3 and Comparative Examples 1, 2, 3 and 4 are summarized in Table 1.

TABLE 1

| Materials | Example | | | Comparative Example | | | |
|---|---|---|---|---|---|---|---|
| | 1 | 2 | 3 | 1 | 2 | 3 | 4 |
| PEG-Mn-SOD | 0.01 | | 0.005 | 0.01 | 0.01 | 0.01 | |
| Mn-SOD | | 0.01 | 0.005 | | | | |
| Manganese chloride (tetrahydrate) | 0.1 | 0.1 | 0.1 | | | | 0.1 |
| Iron(III) chloride (hexahydrate) | | | | | 0.1 | | |
| Glycerin | | | | | | 10.0 | |
| Ethanol | 3.0 | 3.0 | 3.0 | 3.0 | 3.0 | | 3.0 |
| Citric acid (monohydrate) | 0.03 | 0.03 | 0.03 | 0.03 | 0.03 | 0.03 | 0.03 |
| Disodium hydrogen phosphate (dihydrate) | 0.74 | 0.74 | 0.74 | 0.74 | 0.74 | 0.74 | 0.74 |
| Perfume | 0.08 | 0.08 | 0.08 | 0.08 | 0.08 | 0.08 | 0.08 |
| Purified water | 96.04 | 96.04 | 96.04 | 96.14 | 96.04 | 89.14 | 96.05 |

Method of production]

In each example, all the ingredients specified in Table 1 were mixed up together at room temperature to attain uniform dissolution and give a skin lotion. The skin lotions obtained in the corresponding examples were subjected to the following tests (1) and (2). (1)Stability test "Method and results"

Samples

The skin lotions of Examples 1, 2 and 3 and the skin lotions of Comparative Examples 1, 2 and 3.

Test method

Each sample was subjected to enzyme activity assay before and after one-month standing at 40° C. The assay was performed by the nitro blue tetrazolium (NBT) reduction method of Hanada et al. [Toshiro Hanada et al., Rinsho Kensa Kiki Shiyaku (Journal of Clinical Laboratory Instruments and Reagents), 8 (3), 629 (1985)].

The enzyme activity (A) of each sample directly after preparation and the enzyme activity (B) thereof after one-month standing at 40° C. were respectively determined.

Percentage (%) of residual enzyme activity $= B/A \times 100$

The results are as shown in Table 2.

TABLE 2

| Sample | Residual enzyme activity (%) |
|---|---|
| Example 1 | 95 |
| 2 | 91 |
| 3 | 93 |
| Comparative Example 1 | 47 |
| 2 | 23 |
| 3 | 68 |

As is evident from the data given in Table 2, the residual enzyme activity percentages for the aqueous skin lotions containing the manganese salt in combination with Mn-SOD and/or modified Mn-SOD were not less than 90%, indicating very high levels of stability.

On the other hand, the residual enzyme activity percentages for the skin lotion of Comparative Example 1, which contained the modified Mn-SOD alone, and the skin lotion of Comparative Example 2, which contained an iron salt in combination with the modified Mn-SOD, were considerably lower as compared with the skin lotions of Examples 1 to 3.

The residual enzyme activity percentage for the lotion of Comparative Example 3, which contained a water-soluble polyhydric alcohol in combination with the modified Mn-SOD, showed an improvement when compared with the lotion of Comparative Example 1 but the extent of improvement was still unsatisfactory.

On the contrary, the preparations of Examples 1 to 3 showed further improvements in enzyme stability as compared with the preparation of Comparative Example 3 and were thus found to have satisfactory stability for their use as external skin preparation. (2) Test for skin roughening reducing effect "Method and results"

Samples

The skin lotion of Example 1 and the skin lotion of Comparative Example 4.

Method

Thirty subjects of middle or advanced age who were apt to have a roughening skin were divided into two groups. In one group, the skin lotion of Example 1 was applied and, in another, the skin lotion of Comparative Example 4 was applied. Thus, a cut puff (5 cm × 6.5 cm; product of Unicharm Co., Ltd.) was soaked with 2 ml of either sample and used for application of the sample to the skin of each subject twice (morning and evening) a day for consecutive 4 weeks and the skin conditions before and after testing were evaluated.

The results are as shown in Table 3.

Improvement rating was made according to the following criteria.

TABLE 3

| Sample | Skin roughening reducing effect | | | |
|---|---|---|---|---|
| | ++ | + | ± | Worsening |
| Example 1 | 1 | 10 | 4 | 0 |
| Comparative Example 4 | 0 | 7 | 8 | 0 |

++: Marked improvement, with the skin being nearly normal.
+: Slight improvement, with the degree of desquamation being slight.
±: No significant improvement.

As is evident from the data shown in Table 3, the skin lotion of Example 1, which contained the modified Mn-SOD, was superior in skin roughening reducing effect to the skin lotion of Comparative Example 4.

As is evident from the foregoing description, the external skin preparation according to the invention is a very excellent one, showing good stability with a high residual enzyme activity percentage and further showing an antagonizing effect on the skin roughening otherwise caused by Mn-SOD.

Some practical examples of the aqueous external skin preparation according to the invention are shown in the following.

Example 4 Lotion of extemporaneous preparation type

| Product A | |
|---|---|
| Formulation (1) | |
| Squalane | 0.1 |
| δ-Tocopherol | 0.02 |
| Methyl p-hydroxybenzoate | 0.1 |
| Polyoxyethylene (50) hardened castor oil | 0.8 |
| Perfume | 0.009 |
| Formulation (2) | |
| 1,3-Butylene glycol | 4.0 |
| Purified water | 86.17 |
| Product B | |
| Formulation (3) | |
| Citric acid (monohydrate) | 0.03 |
| Disodium hydrogen phosphate (dihydrate) | 0.67 |
| Manganese acetate (tetrahydrate) | 0.1 |
| Modified Mn-SOD | 0.001 |
| Purified water | 8.0 |

[Method of production]

The ingredients of the above formulation (1) are mixed up by stirring at room temperature to attain uniform dissolution. Separately, the ingredients of the above formulation (2) are treated in the same manner. The solution derived from the ingredients of formulation (2) is added to the solution derived from the ingredients of formulation (1) for solubilization. The resulting mixture is packed into containers to give product A.

The ingredients of the above formulation (3) are mixed up by stirring for uniform dissolution and the resulting mixture is packed into containers to give product B.

[Method of use]

As appropriate amount of product B is taken in the palm of the hand, about 10 volumes of product A is added, and both the products are mixed together by means of a finger. The mixture is applied to the skin by proper massaging movements.

Example 5 Nutritive cream

| Formulation (1) | |
|---|---|
| Squalane | 16.0 |
| Cetanol | 4.0 |
| Lipophilic glycerin monostearate | 1.0 |
| Polyethylene glycol (25E.O.) monostearate | 2.5 |
| Formulation (2) | |
| Glycerin | 3.0 |
| Citric acid (monohydrate) | 0.02 |
| Disodium hydrogen phosphate (dihydrate) | 0.5 |
| Manganese chloride (tetrahydrate) | 0.5 |
| Purified water | 72.37 |
| Formulation (3) | |
| Mn-SOD | 0.1 |
| Perfume | 0.01 |

[Method of production]

The ingredients of the above formulation (1) are heated at 70° C. to achieve dissolution. The ingredients of the above formulation (2) are treated in the same manner. The solution of the ingredients of formulation (2) is added portionwise to the solution of the ingredients of formulation (1) with stirring for emulsification.

The resulting mixture is cooled to 40° C. with stirring, then the ingredients of the above formulation (3) are added, and the whole mixture is further cooled to 30° C. The mixture is filled into containers to give a The mixture is filled into containers to give a product nutritive cream.

Example 6 Ointment

| Formulation (1) | |
|---|---|
| Liquid paraffin | 65.0 |
| White petrolatum | 6.0 |
| Polyoxyethylene (20E.O.) sorbitan monostearate | 6.0 |
| Beeswax | 3.0 |
| Formulation (2) | |
| Glycerin | 10.0 |
| Purified water | 5.0 |
| Formulation (3) | |
| PEG-Mn-SOD | 0.05 |
| Manganese chloride (tetrahydrate) | 0.95 |
| Purified water | 4.0 |

[Method of production]

The ingredients of the above formulation (1) are mixed together with heating and stirring The ingredients of the above formulation (2) are then added. The resulting mixture is cooled to 40° C. with stirring, the ingredients of the above formulation (3) are further added, and the whole mixture is cooled to 30° C.

The mixture is filled into containers to give a product ointment.

What is claimed is:

1. An aqueous external skin preparation which contains, as essential components thereof, (a) 0.1 to 20,000 units per gram as expressed in terms of potency of manganese-containing superoxide dismutase and/or a polyalkylene glycol- or polysaccharide-bound modification of manganese-containing superoxide dismutase and (b) 0.0001 to 10% by weight based on said external skin preparation of a physiologically acceptable water-soluble manganese salt.

2. An aqueous external skin preparation according to claim 1, wherein said manganese-containing superoxide dismutase is derived from a microorganism.

3. A method of producing an aqueous external skin preparation, which comprises mixing (a) 0.1 to 20,000 units per gram as expressed in terms of potency of manganese-containing superoxide dismutase and/or polyalkylene glycol- or polysaccharide-bound modification of manganese-containing superoxide dismutase and (b) 0.0001 to 10% by weight based on said external skin preparation of a physiologically acceptable water-soluble manganese salt as essential components with other ingredients.

4. A method according to claim 3, wherein the manganese-containing superoxide dismutase is produced from a microorganism.

5. A method of stabilizing manganese-containing superoxide dismutase and/or polyalkylene glycol- or polysaccharide-bound modification of manganese-containing superoxide dismutase in an aqueous system the content of manganese-containing superoxide dismutase and/or polyalkylene glycol- or polysaccharide-bound modification of manganese-containing superoxide dismutase being 0.1 to 20,000 units per gram as expressed in terms of potency which comprises incorporating into the aqueous system 0.001 to 10% by weight of the aqueous system of a physiologically acceptable water-soluble manganese salt.

* * * * *